United States Patent [19]
Minden et al.

[11] Patent Number: 6,127,134
[45] Date of Patent: Oct. 3, 2000

[54] DIFFERENCE GEL ELECTROPHORESIS USING MATCHED MULTIPLE DYES

[75] Inventors: Jonathan Minden; Alan Waggoner, both of Pittsburgh, Pa.

[73] Assignee: Carnegie Mellon University, Pittsburgh, Pa.

[21] Appl. No.: 08/425,480

[22] Filed: Apr. 20, 1995

[51] Int. Cl.[7] .......................... G01N 33/53; G01N 33/00; C12Q 1/00; C07K 1/00
[52] U.S. Cl. ..................... 435/7.2; 435/4; 435/6; 436/800; 436/63; 436/80; 530/344; 530/412
[58] Field of Search ..................... 435/47.2, 6; 436/800, 436/63, 86; 530/344, 412

[56] References Cited

U.S. PATENT DOCUMENTS

| | | |
|---|---|---|
| 4,774,339 | 9/1988 | Haugland et al. . |
| 4,855,225 | 8/1989 | Fung et al. . |
| 4,874,492 | 10/1989 | Mackay . |
| 5,242,796 | 9/1993 | Prober et al. . |
| 5,248,782 | 9/1993 | Haugland et al. . |
| 5,268,486 | 12/1993 | Waggoner et al. . |
| 5,274,113 | 12/1993 | Kang et al. . |
| 5,296,599 | 3/1994 | Cohen et al. . |
| 5,307,148 | 4/1994 | Kambara et al. . |
| 5,312,921 | 5/1994 | Glazer et al. . |
| 5,338,854 | 8/1994 | Kang et al. . |
| 5,364,764 | 11/1994 | Haugland et al . |
| 5,654,419 | 8/1997 | Mathies et al. . |

FOREIGN PATENT DOCUMENTS

| | | |
|---|---|---|
| 0 272 007 A2 | 6/1988 | European Pat. Off. . |
| 5-322771 | 12/1993 | Japan . |
| WO 92/14747 | 9/1992 | WIPO . |

OTHER PUBLICATIONS

Amersham Life Science Products Catalogue (1991) p. 61, Illinois USA "Rainbow Protein Molecular Weight Markers".

L. M. Smith et al., "Flourescence Detection In Automated DNA Sequence Analysis" Nature vol. 321, No. 6071, pp. 674–679 (Jun. 12, 1986), p. 674–75.

Juan F. Santaren et al., Identification of Drosophila Wing Imaginal Disc Proteins by Two–Dimensional Gel Analysis and Microsequencing, Experimental Cell Research 206, 220–226 (1993).

James I. Garrels, Two–Dimensional Gel Electrophoresis and Computer Analysis of Proteins Synthesized by Clonal Cell Lines, The Journal of Biological Chemistry, vol. 254, No. 16, Issue of Aug. 25, pp. 7961–7977, (1979). Printed in U.S.A.

Peter Jackson et al. Rapid imaging, using a cooled charged–coupled–device, of fluorescent two–dimensional polyacrylamide gels produced by labelling proteins in the first–dimensional isoelectri focusing gel with the fluorophore 2–methoxy-2,4–diphenyl-3 (2H) furanone, Electrophoresis, pp. 330–339, (1988).

Patrick H. O'Farrell, High Resolution Two–Dimensional Electrophoresis of Proteins, The Journal of Biological Chemistry, vol. 250, No. 10, Issue of May 25, pp. 4007–4021, Printed in U.S.A.

Valerie E. Urwin et al., A Multiple High–Resolution Mini Two–Dimensional Polyacrylamide Gel Electrophoresis Systems: Imaging Two–Dimensional Gels using a Cooled Charge–Coupled Device after Staining with Silver or Labeling with Fluorophore, Anyalyical Biochemistry 195, pp. 30–37 (1991).

*Primary Examiner*—Nita Minnifield
*Attorney, Agent, or Firm*—Kirkpatrick & Lockhart LLP

[57] ABSTRACT

A process and a kit are provided for detecting differences in two or more samples of protein. Protein extracts are prepared, for example, from each of a different group of cell samples to be compared. Each protein extract is labeled with a different one of a luminescent dye from a matched set of dyes. The matched dyes have generally the same ionic and pH characteristics but emit light at different wavelengths to exhibit a different color upon luminescence detection. The labeled protein extracts are mixed together and electrophoresed together. The gel is observed to detect proteins unique to one sample or present in a greater ratio in one sample than in the other. Those unique or excess proteins will fluoresce the color of one of the dyes used. Proteins common to each sample migrate together and fluoresce the same.

18 Claims, 4 Drawing Sheets

DIFFERENCE GEL ELECTROPHORESIS USING MATCHED MULTIPLE DYES

BACKGROUND OF THE INVENTION

1. Field of the Invention

The present invention relates to a process for detecting differences in the protein composition of cells and cell extracts, and more particularly, to a process utilizing a matched pair of labeling reagents for detecting such differences.

2. Background of the Invention

Researchers studying various aspects of cell biology use a variety of tools to detect and monitor differences in cell structure, function and development. An essential part of studying cells is studying the differences and similarities in the protein composition between the different cell types, stages of development and condition. Determining differences in the protein content between normal and cancerous cells or wild type and mutant cells, for example, can be a valuable source of information and a valuable diagnostic tool.

Mixtures of proteins can be separated into individual components according to differences in mass by electrophoresing in a polyacrylamide gel under denaturing conditions. One dimensional and two dimensional gel electrophoresis have become standard tools for studying proteins. One dimensional SDS (sodium dodecyl sulfate) electrophoresis through a cylindrical or slab gel reveals only the major proteins present in a sample tested. Two dimensional polyacrylamide gel electrophoresis (2D PAGE), which separates proteins by isoelectric focusing, i.e., by charge, in one dimension and by size in the second dimension, is the more sensitive method of separation and will provide resolution of most of the proteins in a sample.

The proteins migrate in one- or two-dimensional gels as bands or spots, respectively. The separated proteins are visualized by a variety of methods; by staining with a protein specific dye, by protein mediated silver precipitation, autoradiographic detection of radioactively labeled protein, and by covalent attachment of fluorescent compounds. The latter method has been heretofore only able to be performed after the isoelectric focusing step of 2D PAGE. Immediately following the electrophoresis, the resulting gel patterns may be visualized by eye, photographically or by electronic image capture, for example, by using a cooled charge-coupled device (CCD).

To compare samples of proteins from different cells or different stages of cell development by conventional methods, each different sample is presently run on separate lanes of a one dimensional gel or separate two dimensional gels. Comparison is by visual examination or electronic imaging, for example, by computer-aided image analysis of digitized one or two dimensional gels.

Two dimensional electrophoresis is frequently used by researchers. O'Farrell, P. H., "High resolution two-dimensional electrophoresis of proteins", Journal of Biological Chemistry, 250:4007–4021 (1975), separated proteins according to their respective isoelectric points in the first dimension by the now well known technique of isoelectric focusing and by molecular weight in the second dimension by discontinuous SDS electrophoresis. Garrels, J. I., "Two-dimensional Gel Electrophoresis and Computer Analysis of Proteins Synthesized By Clonal Cell Lines", Journal of Biological Chemistry, Vol. 254, No. 16, 7961–7977 (1979), used a two dimensional gel electrophoresis system to study the pattern of protein synthesis in nerve cells and glial cells. Garrels conducted a comparative analysis of data from multiple samples to correlate the presence of particular proteins with specific functions. Computerized scanning equipment was used to scan a section of the gel fluorogram, detect the spots and integrate their densities. The information was stored and plotted according to intensity in each of several different scans.

Urwin, V. E. and Jackson, P., "A multiple High-resolution Mini Two-dimensional Polyacrylamide Gel Electrophoresis System: Imaging Two-dimensional Gels Using A Cooled Charge-Coupled Device After Staining With Silver Or Labeling With Fluorophore", Analytical Biochemistry 195:30–37 (1991) describes a technique wherein several isoelectric focusing (IEF) gels were used to separate proteins by charge, then loaded onto a gradient slab gel such that the IEF gels were positioned end to end along the top of the slab gel. The gels were then electrophoresed. The resulting protein spots were visualized either by staining the second dimensional slab gel with silver or by fluorescent labeling following the isoelectric focusing step. Labeling must take place after the first electrophoresis, i.e., the isoelectric focusing because the presence of the fluorescein label on the protein changes the isoelectric point of the protein when subjected to electrophoresis. In addition, the label attaches to a sulfur on the protein forming an unstable bond which would tend to break during isoelectric focusing if the label is attached prior to the electrophoresis step. An article by Santaren, J. et al., "Identification of Drosophila Wing Imaginal Disc Proteins by Two-Dimensional Gel Analysis and Microsequencing", Experimental Cell Research 206: 220–226 (1993), describes the use of high resolution two dimensional gel electrophoresis to identify proteins in *Drosophila melanogaster*. The dry gel was exposed to X-ray film for five days. The developed X-ray film is analyzed by a computer to determine the differences in the samples.

Two dimensional gel electrophoresis has been a powerful tool for resolving complex mixtures of proteins. The differences between the proteins, however, can be subtle. Imperfections in the gel can interfere with accurate observations. In order to minimize the imperfections, the gels provided in commercially available electrophoresis systems are prepared with exacting precision. Even with meticulous controls, no two gels are identical. The gels may differ one from the other in pH gradients or uniformity. In addition, the electrophoresis conditions from one run to the next may be different. Computer software has been developed for automated alignment of different gels. However, all of the software packages are based on linear expansion or contraction of one or both of the dimensions on two dimensional gels. The software cannot adjust for local distortions in the gels.

The object of the present invention is to eliminate the problems associated with gel distortions and to provide a simple, relatively fast and reliable method of comparing and contrasting the protein content of different samples.

BRIEF SUMMARY OF THE INVENTION

The foregoing objects have been achieved by the process of the present invention which provides a method of comparing multiple samples of cell extract. The method includes the steps of preparing samples of cell extract from each of at least two different groups of cells and exposing each sample of extract to a different one of a set of matched luminescent dyes to covalently bind the dye to the extract to label the extract. Each dye within the set of dyes is capable of covalently binding the extract, has generally the same ionic and pH characteristics as all other dyes within the set of dyes and emits light at a wavelength sufficiently different from all the other dyes within the set of dyes to present different colored light. The method of the invention further includes the steps of quenching the binding of the dye to the extract, mixing the samples of labeled extract to form a mixture, electrophoresing the mixture to separate the extract components and detecting the difference in fluorescence intensity among the separated labeled components by luminescence detection.

In the preferred process of the present invention, the differences, if any, between multiple samples of proteins extracted for example, from different cells, are detected by labeling each sample of such proteins with a different one of a set of matched luminescent dyes. The matched dyes have generally the same ionic and pH characteristics but absorb and/or fluoresce light at different wavelengths, producing a different color fluorescence. In addition, the dyes should be similar in size. After an incubation period sufficient to permit the formation of covalent bonds between the dye and a plurality of attachment sites on the proteins in the cell extract, preferably reacting with up to about 2% of the total available attachment sites, the free reactive dye is then quenched to prevent further reaction with the proteins, the labeled samples are then mixed together and co-electrophoresed on a single gel. The proteins common to each sample comigrate to the same position. Proteins which are different will migrate alone to different locations on the gel and will fluoresce different colors, thereby identifying which initial sample has one or more proteins which differ from the other initial sample or samples.

The invention also includes a kit for performing the method of the present invention. The kit includes the matched set of dyes, and may also include a quench material for stopping the reaction between the protein and the dye, and the electrophoresis gels.

DESCRIPTION OF THE DRAWINGS

The file of this patent contains at least one drawing executed in color. Copies of this patent with color drawings will be provided by the Patent and Trademark Office upon request and payment of necessary fee.

DETAILED DESCRIPTION OF THE PREFERRED EMBODIMENTS

The process of the present invention employs a matched set of dyes wherein each dye in the set is generally equal to the other dyes in ionic and pH characteristics, and chemical reactivity for covalent attachment to proteins, yet fluoresces at a different wavelength, thereby exhibiting a different color luminescence when viewed. The dyes are preferably roughly equal in molecular weight, but need not be. Each one of the dyes within the matched set of dyes is used to label proteins in a different one of a set of different samples of cell extract so that each cell extract sample is labeled with a different dye within the set of dyes. After labeling, the extracts are mixed and electrophoresed in the same gel, either by one or two dimensional electrophoresis.

Figure 1:
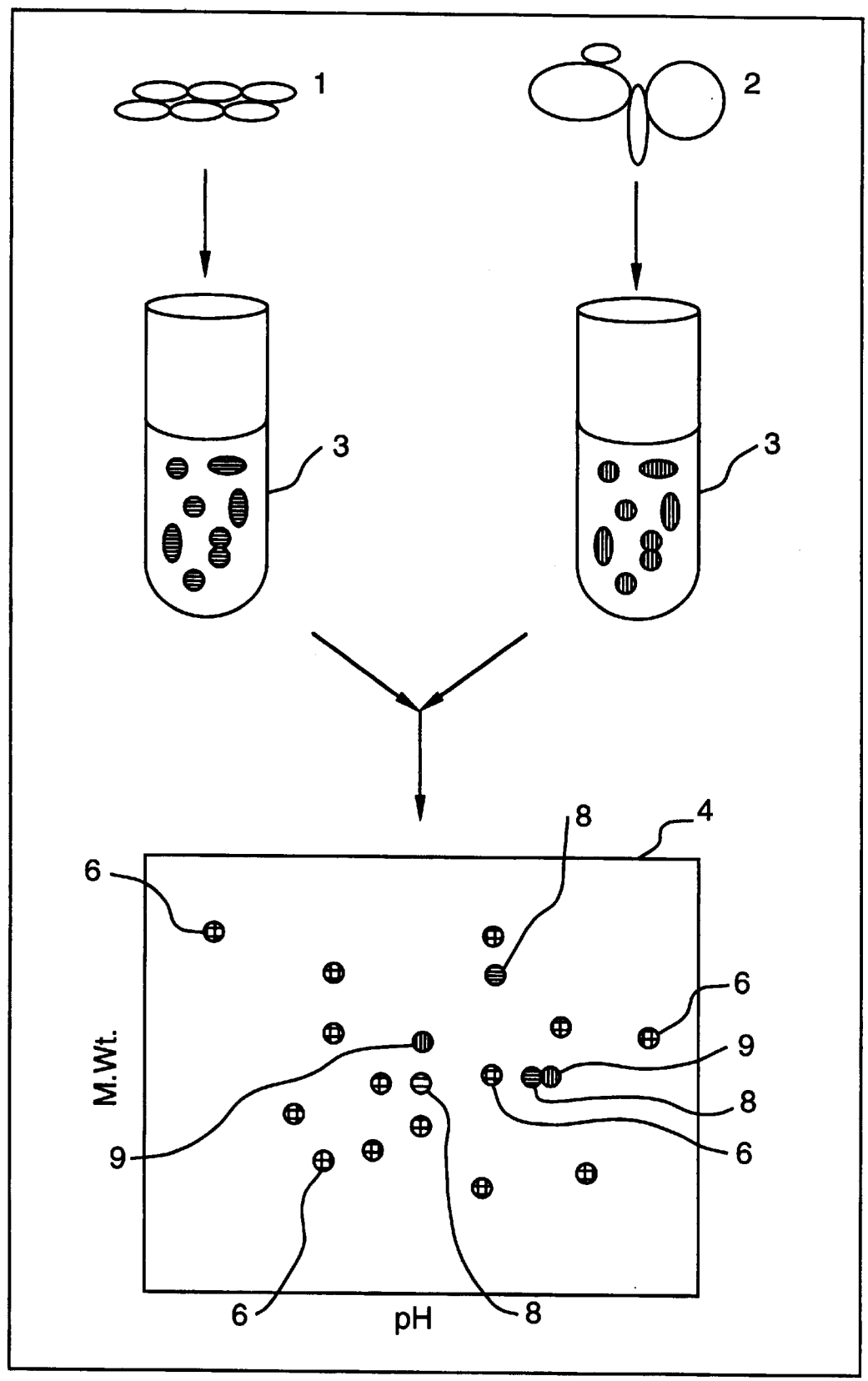
FIG. 1 is a schematic diagram of the process of the present invention.

With reference to the schematic diagram of FIG. 1, a first cell extract is prepared by known techniques from a first group of cells, then labeled with the first dye of a matched pair of dyes. A second cell extract is prepared by known techniques from a second group of cells then labeled with the second dye of the matched pair of dyes. To label the cell extract mixture, the reactive form of the dye and the protein extract are incubated for a period of time sufficient to allow for the formation of a covalent bond between the reactive form of the dye and potential attachment or binding sites on the proteins in the extract. The period of time is generally from 15 to 30 minutes, depending on the temperature. The temperature range is generally from about 0° C. to 25° C. The reaction between the dye and the proteins may be quenched after a sufficient percentage of available binding sites on the protein molecule are covalently bound to the dye. Any suitable known quenching material may be used.

The first and second group of cells can be any two sets of cells the protein content of which one wishes to compare or contrast. For example, the first group of cells can be the wild-type, or normal, cells, and the second group of cells can be mutant cells from the same species. Alternatively, the first group of cells can be normal cells and the second group can be cancerous cells from the same individual. Cells from the same individual at different stages of development or different phases of the cell cycle can be used also. The cells from a developing embryo, from the ventral furrow of *Drosophila melanogaster*, for example, can be harvested as the first group of cells and cells that develop adjacent to the ventral furrow cells can be harvested as the second group of cells. The differences in protein composition between cells of the same type from different species can also be the subject of study by the process of the present invention. In addition, the process of the present invention can be used to monitor how cells respond to a variety of stimuli or drugs. All of the events that might alter cell behavior as expressed through protein changes can be detected without the need and expense of high precision 2D PAGE systems. Those skilled in the art will recognize that the proteins for comparison may also be derived from biological fluids, such as serum, urine, or spinal fluid.

The labeled samples are mixed and, as illustrated in FIG. 1, applied in measured aliquots to one gel, then preferably subjected to 2D PAGE. One dimensional SDS electrophoresis can be used instead of 2D PAGE. The procedures for running one dimensional and two dimensional electrophoresis are well known to those skilled in the art.

Proteins that the two cell groups have in common form coincident spots. The ratio of the fluorescent intensity between identical proteins from either group will be constant for the vast majority of proteins. Proteins that the two groups do not have in common will migrate independently. Thus, a protein that is unique or of different relative concentration to one group will have a different ratio of fluorescence intensity from the majority of protein spots, and will produce a color specific for one or the other of the protein extracts, depending on the label used. For example, the proteins that are in the first sample may be labeled red, while the second group is labeled blue. Under conditions where exactly equal amounts of protein from each group is mixed together and run on the same gel the ratio of fluorescence intensity will be one for the majority of proteins. Those proteins that are distinct to one or the other group will have a fluorescence intensity ratio less than or greater than one, depending on the order or ratioing.

The gel can be analyzed by a two wavelength fluorescence scanner, by a fluorescent microscope or by any known means for detecting fluorescence. Gel analysis can be completely automated by means of computer aided identification of protein differences. Using an electronic detection system such as a laser scanning system with a photo multiplier tube or a charged-coupled device (CCD) camera and a white light source, two electronic images are made of the wet gel using different known filter sets to accommodate the different spectral characteristics of the labels. One image views fluorescence of the first dye using a first filter appropriate to filter out all light except that emitted at the wavelength of the first dye and the other image views fluorescence of the second dye using a second filter, appropriate to filter out all light except that emitted at the wavelength of the second dye. Exposure is about 5 to 500 seconds. The differences in the samples can be identified, either during electrophoresis or in less than ½ hour following electrophoresis. Several software packages are commercially available which will either subtract the first image from the second to identify spots that are different, or, alternatively, the images may be divided to leave only the spots not common to both images. In subtracting the images, like spots will cancel each other, leaving only those that are different. In ratio analysis, like spots will provide a value of one. Differences will result in values greater than one less than one.

In conventional analysis, a control is run with known proteins for the cell type being studied. The known spots on the sample gel have to be identified and marked, compared to the control and the second gel to determine differences between the two gels. In the present invention, there is only one gel so no marking is necessary. In addition, the software used on conventional processes for alignment of different gels prior to comparing and contrasting protein differences does not correct for local distortions and inconsistencies between two or more gels. The process of the present invention eliminates the need for such correction because the extracts for all samples to be tested are mixed and run on the same gel. Any gel distortions are experienced equally by each sample.

Selection and synthesis of the matched set of dyes is important. In the process of the present invention, the fluorescent dyes are covalently coupled to proteins, preferably via lysine residues of the proteins, but coupling may also be to sulfhydryl or carboxylic acid groups in the proteins. Regulation of the pH of proteins to force attachment of labels at one amino acid residue to the exclusion of other amino acids is a well known technique, as set forth in R. Baker, Organic Chemistry of Biological Components, (Prentice Hall, pub. 1971). For analysis of proteins, a plurality of attachment sites are labeled. The optimum percentage of attachment sites labeled will depend on the dyes chosen. When the preferred dyes specifically discussed hereinbelow are used, preferably no more than 2% of the attachment sites and more preferably, slightly less than 1%, are labeled, to avoid rendering the protein insoluble. Thus, where a typical protein is composed of about 7% lysines, there will be less than one modified amino acid per one thousand. A typical protein is composed of about 450 amino acids. When lysine is the attachment site, the covalent linkage destroys the positive charge of the primary amine of the lysine. Because isoelectric focusing depends on charge, it is important to compensate for the charge loss. A basic residue should remain basic. Changing the $pK_a$ of one residue per protein by as much as 3 can be tolerated, provided the basicity or acidity of the modified residue, as the case may be, is not altered. Dyes like rhodamine and fluorescein are not suitable because of the difference in charge.

The first group of dyes evaluated were the fluorescent cyanine dyes described in Mujumdar, R. B. et al., "Cyanine dye labeling reagents containing isothiocyanate groups", Cytometry 10:11–19 (1989) and Waggoner et al., U.S. Pat. No. 5,268,486 entitled "Method for labeling and detecting materials employing arylsulfonate cyanine dyes" issued in 1993 and incorporated herein by reference. The cyanine dyes have the following general structure.

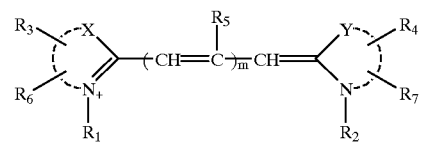

where X and Y can be O, S or $(CH_3)_2$—C, m is an integer from 1 to 3 and at least one of $R_1$, $R_2$, $R_3$, $R_4$, $R_5$, $R_6$ or $R_7$ is a reactive group which reacts with amino, hydroxy or sulfhydryl nucleophiles. The dotted lines represent the carbon atoms necessary for the formation of one ring to three fused rings having 5 to 6 atoms in each ring. $R_3$, $R_4$, $R_6$ and $R_7$ are attached to the rings. The reactive moiety can be any known reactive group. Reactive groups that may be attached directly or indirectly to the chromophore to form $R_1$, $R_2$, $R_3$, $R_4$, $R_5$, $R_6$ or $R_7$ groups may include reactive moieties such as groups containing isothiocyanate, isocyanate, monochlorotriazine, dichlorotriazine, mono- or di-halogen substituted pyridine, mono- or di-halogen substituted diazine, maleimide, aziridine, sulfonyl halide, acid halide, hydroxysuccinimide ester, hydroxysulfosuccinimide ester, imido ester, hydrazine, azidonitrophenyl, azide, 3-(2-pyridyl dithio)-proprionamide, glyoxal and aldehyde.

The cyanine dyes described in the Waggoner et al. patent were the fluorophors of choice because of their intrinsic positive charge. The cyanines attach to the protein via the activated ester of hexanoic acid. While the coupling destroys the charge of the lysine side chain, the intrinsic charge in the dye compensates. It in effect moves the charge away from the protein molecule but maintains the same overall charge within the sample to be electrophoresed. In the cyanine dye molecule, two functionalized indole rings are connected via a polyene linker. The spectral characteristics of cyanine dyes can be easily modulated by simply changing the length of the linker between the indole rings of the dye. A longer or shorter linker length will result in fluorescence at different wavelengths and thus, different colors. However, changing the length of the linker changes the molecular mass of the dye. Since electrophoresis depends also on the mass of the proteins, the effect of the dye on a protein's mass can also be of concern. Because the proteins are labeled before electrophoresing, the mass of the dye attached to the protein must not significantly alter the relative differences in the molecular weights of the various proteins in the extracts. Molecular weight is not critical, however, because only a relatively small number of sites on the protein are labeled.

As indicated above, preferably less than 1%, up to about 2% of the possible attachment sites on the proteins are labeled. If more are labeled, maintaining generally equal molecular weights for the dyes within the set of matched dyes becomes a greater concern.

The difference in molecular weight caused by changing the linker length in the fluorescent cyanine dyes can be compensated for by modulating the size of an aliphatic chain $R_1$ or $R_2$, attached to one of the dye's indole rings. One of $R_1$ or $R_2$ must be a reactive group. These design constraints led to the modification of the cyanines and the development of a dye of the general formula.

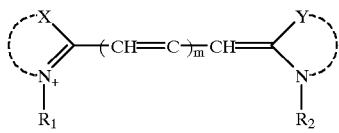

wherein X and Y equal S, O, or $CH_3$—C—$CH_3$, m is an integer from 1 to 3 and either $R_1$ or $R_2$ is a reactive group capable of covalently binding to the protein in the cell extract, such as the reactive groups described above for the unmodified cyanine dyes. The dotted lines represent 1, 2 or 3 fused rings having 5 or 6 carbon atoms in each ring. Each side should balance the other side.

An example of a matched pair of dyes developed according to the general formula follows:

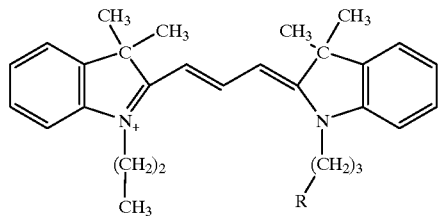

(Propyl Cy-3-NHS) which fluoresces red and,

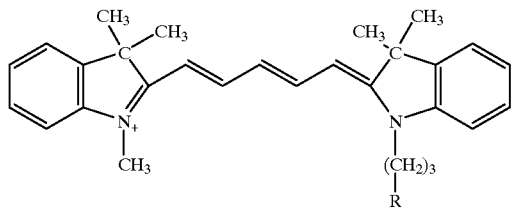

(Methyl Cy-5-NHS) which fluoresces far red in the spectrum wherein R is a reactive group. As stated above, O or S or a combination thereof can be placed in the X and Y positions in place of $(CH_3)_2C$—.

The cyanine dyes are one choice for the matched set of dyes of the present invention. Other dye compounds may be used in place of the cyanines, such as dipyrromethene boron difluoride dyes, the derivatized 4,4-difluoro-4-bora-3a,4a,-diaza-S-indacene dyes, described in U.S. Pat. No. 4,774,339 to Haugland et al. and incorporated herein by reference, which are sold by Molecular Probes, Inc. under the trademark BODIPY®. The BODIPY® dyes, which have no net charge, are covalently linked to lysine side chains using an activated n-hydroxysuccinimidyl ester which forms an amide bond. The result is the loss of the lysine positive charge. Therefore, a positively charged linker group is used in the matched dyes of the invention to replace the lost primary amine with the linker's tertiary amine. The procedures for making BODIPY® dyes are described in U.S. Pat. No. 4,774,339. Addition of the positively charged linker is by techniques well known to those skilled in the art. A linker can be designed with three functional groups; (1) to react with the BODIPY®-NHS ester, (2) to carry the desired charge, and (3) to be activated so that the BODIPY®-linker construct will react with specific amino acid residues of the proteins in the extract.

The major considerations for the matched set of dyes are the maintenance of charge and distinct and different spectral characteristics. Any neutral dyes with a positive linker or any positively charged dyes, preferably each having a +1 charge, that otherwise satisfy the requirements described herein can serve as the dyes in the matched set of dyes of the present invention. Roughly equal molecular weight in the samples of labeled protein is desirable, but as explained above, not critical. The intrinsic positive charge of cyanine dyes is advantageously used in the preferred embodiment to replace the positive charge of lysine. The $pK_a$ of cyanines and lysine are rather different; however, conditions were selected for dye:protein ratio to be less than one. This low level of labeling ensures that there will be negligible changes in the protein's migration on two-dimensional electrophoresis gels. Dyes may be used which match the $pK_a$ of lysine more closely. Alternately, dyes that modify other amino acid residues may be used, provided the amino acid's ionic characteristics are preserved by the modification. Instead of a lysine, the attachment site on the protein may be a sulfhydryl or carboxylic group. When a sulfhydryl group is the attachment site on the protein, the corresponding attachment site on the dye is an iodoalkyl group. When a carboxylic acid group is the attachment site on the protein, the corresponding attachment site on the dye is a chloroketone or a carbodiimide.

It is anticipated that the method of the present invention also can be used to detect the presence of different nucleic acids in different samples. The charge of nucleic acids is very negative. The addition of the dye does not therefore alter the overall charge in nucleic acids so the choice of the matched set of dyes does not have to compensate for charge loss when nucleic acid analysis is contemplated. To facilitate attachment of the dye, nucleic acids can be modified to have a free amino acid coming from the nucleic acid nucleus by techniques known to those skilled in the art. A lysine would be suitable in this instance also.

EXAMPLE 1

Synthesis of the dyes (Methyl Cy-5 and Propyl Cy-3):

1. Synthesis of indole derivatives (common to both dyes):
4.8 g (30 mmoles) of 2,3,3-trimethyl-(3H)-indole and 35 mmoles of the desired bromoalkyl reagent (6-bromohexanoic acid or 1-bromopropane) in 40 ml of 1,2-dichlorobenzene were heated to 110° C. under nitrogen gas and stirred overnight with refluxing. The product (acid indole, methyl indole, or propyl indole) precipitated as an orangish gum. The supernatant was decanted and the gum was washed several times with ethyl ether. This intermediate was used as is.

2. CY-3 intermediate:
1.5 g (7.5 mmoles) of propyl indole was added to 1.6 g (7.6 mmoles) of N-N' diphenyl formamidine in 20 ml glacial acetic acid and was refluxed for 4 hrs. The solvent was removed under vacuum leaving a deep orange syrup. This intermediate was used as is.

2a. Cy-5 intermediate:
The synthesis of the Cy-5 intermediate is the same as the synthesis of the Cy-3 intermediate in step 2 of the dye synthesis except that 2-methylene-1,3,3-trimethylindoline was used instead of propyl indole and the linker was malonaldehyde dianil. The gummy, bluish intermediate was washed twice with ethyl ether.

3. Cy-3:

2.5 ml of triethylamine and 1.8 ml of anhydrous $Ac_2O$ were added to the intermediate from step 2., and the mixture was boiled for 5 minutes. 1.70 g (5.0 mmoles) of acid indole was added and the mixture was refluxed for two hours. The solvent was removed under vacuum and the products were dissolved in 10 ml of EtOH.

3a. Cy-5:

The preparation of Cy-5 is the same as that of Cy-3 except that the intermediate from step 2a. was used instead of the intermediate from step 2.

4. Purification of the products from steps 3. and 3a.:

Methyl Cy-5 and propyl Cy-3 were separated from contaminating side products by running flash chromatography with a silica gel solid phase and 40% MeOH in dichloromethane as the mobile phase.

5. Activation of carboxyl groups:

The carboxylic acid moiety of each dye was converted into an N-hydroxysuccinimidyl ester by dissolving a quantity of purified material in 5 ml of dry dimethylformamidine (DMF). 1.5 equivalents of N-N' disuccinimidyl carbonate (DSC) was added with 0.1 ml dry pyridine/100 mg dye. The reaction was refluxed at 60° C. for 90 minutes under nitrogen.

EXAMPLE 2

Protein Labeling:

1. Bacterial culture:

Initial experiments were performed on *E. coli* that expressed the chimeric GAL4VP16 protein under the control of the lac promoter as described in Chasman, D. I. et al., "Activation of yeast polymerase II transcription by Herpesvirus VP16 and GAL4 derivatives in vitro", Molecular Cell Biology 9:4746–4749 (1989). Two cultures of bacteria were grown to an $OD_{600}$ of 0.7 at 37° C. in 125 ml of standard LB medium containing 50 μg/ml ampicillin. Isophenylthiogalactopyranoside (IPTG), a non-hydrolyzable analog of lactose, was added to one culture at a final concentration of 1 mM. Both cultures were incubated for an additional 2.5 hours.

2. Protein isolation for two-dimensional gel electrophoresis:

Isolation of protein was as follows. The bacteria was isolated by centrifugation. Each bacterial pellet was washed with sonication buffer containing 5 mM Hepes KOH pH 8.4, 5 mM $Mg(OA_c)2$. The pellet was resuspended in sonication buffer containing 50 μg/ml RNase to a final volume of 100 μl. This was then sonicated in ice until the solution was clear, usually several minutes. DNase was added to 50 μg/ml and the sample was incubated for 30 min at 0° C. Solid urea and CHAPS were added to a final concentration of 8 M and 5% respectively. The sample was taken off the ice and 1 volume of lysis buffer added. The sample was either labeled immediately or stored at −80° C.

3. Protein labeling:

Propyl Cy-3-NHS was added to the first sample and Methyl Cy-5-NHS was added to the second sample of cell extract at a concentration of 2 nmole of dye/50 μg of protein. The dye stock solution was typically 2 mM in dimethyl formamide. The reaction was incubated at 0° C. for 30 minutes. Incubation times may vary from about 15 to about 30 minutes, depending on the temperature and the type of cells being studied. Incubation can be for 15 minutes when the temperature is about 25° C. The temperature should not be above that which will cause the proteins to be degraded. The labeled sample was immediately subjected to isoelectric focusing or stored at −80° C.

4. Protein isolation and labeling for SDS-gel electrophoresis:

Bacteria were grown and isolated by sonication as in step 2. of the protein labeling procedure, except RNase or DNase was not added. The cell extract was directly labeled as in step 3 of the protein labeling procedure. SDS, glycerol, Tris HCl pH 6.8, and bromophenol blue were added to bring the final concentrations to 1%, 10%, 64 mM, and 5 μg/ml, respectively. The sample was then placed in a boiling water bath for 2 minutes and then subjected to electrophoresis.

5. Determination of dye to protein ratio:

In order to prevent solubility problems with labeled proteins, conditions were chosen to only label 1–2% of the lysines in the cell extract. This is based on the assumption that 7% of an average protein's amino acids are lysine. The first step in determining the dye to protein ratio was the removal of free dye by adsorption to SM-2 beads (Bio-Rad). The protein concentration was determined by $OD_{260/280}$. The dye content was determined by OD548 and OD650 for Propyl Cy-3 and Methyl Cy-5, respectively ($\epsilon$=100,000 for both dyes).

EXAMPLE 3

Gel Electrophoresis:

1. Two-dimensional electrophoresis:

High resolution two-dimensional gel electrophoresis was carried out by well known techniques.

2. SDS polyacrylamide gel electrophoresis:

SDS polyacrylamide gel electrophoresis was carried out by known techniques.

EXAMPLE 4

Fluorescence Gel Imaging:

At the end of electrophoresis, the gels were soaked in a solution of 25% methanol and 7% acetic acid. The fluorescently labeled proteins in the gel were imaged in the following manner. Gels were placed on a surface of anodized aluminum and irradiated at an incident angle of 60° with a 300 W halogen lamp housed in a slide projector. The light exiting the projector was passed through 1' diameter bandpass filters (Chroma Technologies, Brattleboro Vt.), 545±10 nm and 635±15 nm for Cy-3 and Cy-5, respectively. The images were collected on a cooled, CCD camera (Photometrics Inc., Tucson Ariz.) fitted with a 50 mm lens (NIKON) and a double bandpass emission filter (Chroma Technologies, Brattleboro Vt.), 587.5±17.5 nm and 695±30 nm for Cy-3 and Cy-5, respectively. The CCD camera was controlled by a MACINTOSH II si computer running Photometrics camera controller software. Image integration time ranged from tenths of seconds to several minutes. The excitation filters were housed in a filter wheel attached to the projector. Two successive images were recorded with irradiation from the two filters without moving the gel.

EXAMPLE 5

Image processing:

The image files were transferred to a Personal Iris 4D/35 (Silicon Graphics Inc., Mountain View Calif.). The image files were then processed using the DELTAVISION™ software (Applied Precision, Mercer Island Wash.). The two schemes were used to determine the differences between the differently labeled samples on the gel:

1. Subtraction:

Each image can be considered as a grid-like array of pixel intensities. These arrays of values can be manipulated by a number of arithmetic operations. Here one image was subtracted from the other. Because the two samples loaded onto the gel were not perfectly balanced for overall fluorescence, one image was multiplied by a balancing constant. This factor was determined arbitrarily so that the number of differences between the samples were kept small.

2. Ratio Imaging:

Here one image was divided by the other. Before this operation was performed the images were first normalized to a common intensity range. This was done by setting the minimum and maximum pixel values of each image to zero and an arbitrarily large value, 4095, the maximum possible output value of the CCD camera employed. Intermediate pixel values were scaled linearly between these values. One image was then divided by the other. A balancing factor was also used here to keep the mean quotient at one. Regions of difference were those with a quotient greater than one.

EXAMPLE 6

Figure 2:
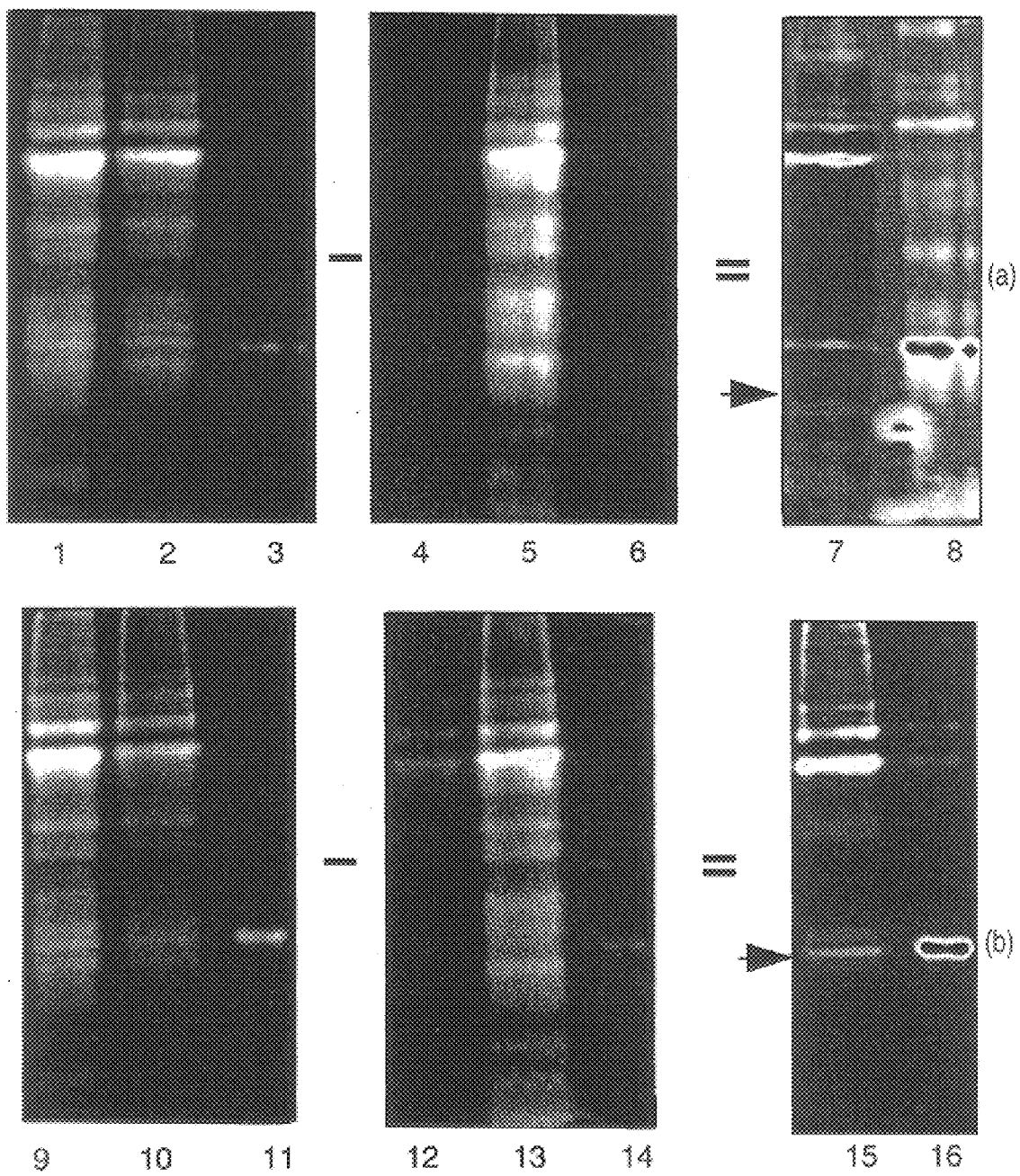
FIGS. 2a and 2b are images of proteins labeled with a preferred matched pair of labels of the present invention run on a single SDS polyacrylamide gel.

1. Difference SDS gel electrophoresis of induced GAL4VP16 expression in bacteria:

FIG. 2 shows images of Propyl Cy-3 and Methyl Cy-5 labeled proteins run on a single SDS polyacrylamide gel. Lanes 1–3 show Cy-3 labeled protein. The samples loaded in there lanes were:

Lane 1. Propyl Cy-3 labeled IPTG-induced bacterial extract.

Lane 2. Propyl Cy-3 labeled IPTG-induced bacterial extract plus Methyl Cy-5 labeled uninduced extract.

Lane 3. Propyl Cy-3 labeled purified GAL4VP16 protein.

Lanes 4–6 show Cy-5 labeled protein. The samples loaded in there lanes were:

Lane 4. Propyl Cy-3 labeled IPTG-induced bacterial extract.

Lane 5. Propyl Cy-3 labeled IPTG-induced bacterial extract plus Methyl Cy-5 labeled uninduced extract.

Lane 6 Propyl Cy-3 labeled purified GAL4VP16 protein. Only Lane 5 showed Cy-5 fluorescence.

Lanes 7 and 8 show the subtracted product of Lane 2–Lane 5 and Lane 3–Lane 6, respectively. The arrows point to the position of GAL4VP16 as confirmed by the position of the purified GAL4VP16 band in lane 8. The identity of the upper bands is not known. However, there are several proteins that are known to be induced by IPTG, including β-galactosidase.

Lanes 9–11 show Cy-5 labeled protein. The samples loaded in these lanes were:

Lane 9. Methyl Cy-5 labeled IPTG-induced bacterial extract.

Lane 10. Methyl Cy-5 labeled IPTG-induced bacterial extract plus Propyl Cy-3 labeled uninduced extract.

Lane 11. Methyl Cy-5 labeled purified GAL4VP16 protein.

Lanes 12–15 show Cy-5 labeled protein. The samples loaded in there lanes were:

Lane 12. Methyl Cy-5 labeled IPTG-induced bacterial extract.

Lane 13. Methyl Cy-5 labeled IPTG-induced bacterial extract plus Propyl Cy-3 labeled uninduced extract.

Lane 14. Methyl Cy-5 labeled purified GAL4VP16 protein. Only Lanes 12–15 all showed some Cy-3 fluorescence. This is due to slight crossover between the bandpass filters. This causes Cy-5 labeled material to appear when excited by Cy-3 light. The converse is not seen. Cy-3 material is not visualized by Cy-5 excitation light. There are two ways to eliminate the crossover effects: design better bandpass filters or computationally remove the Cy-5 contribution to the Cy-3 image by knowing the crossover constant.

Lanes 15 and 16 show the subtracted product of Lane 10–Lane 13 and Lane 11–Lane 14, respectively. The arrows point to the position of GAL4VP16 as confirmed by the position of the purified GAL4VP16 band in Lane 16. The identity of the upper bands is not known. However, there are several proteins that are known to be induced by IPTG, including β-galactosidase.

Figure 3:
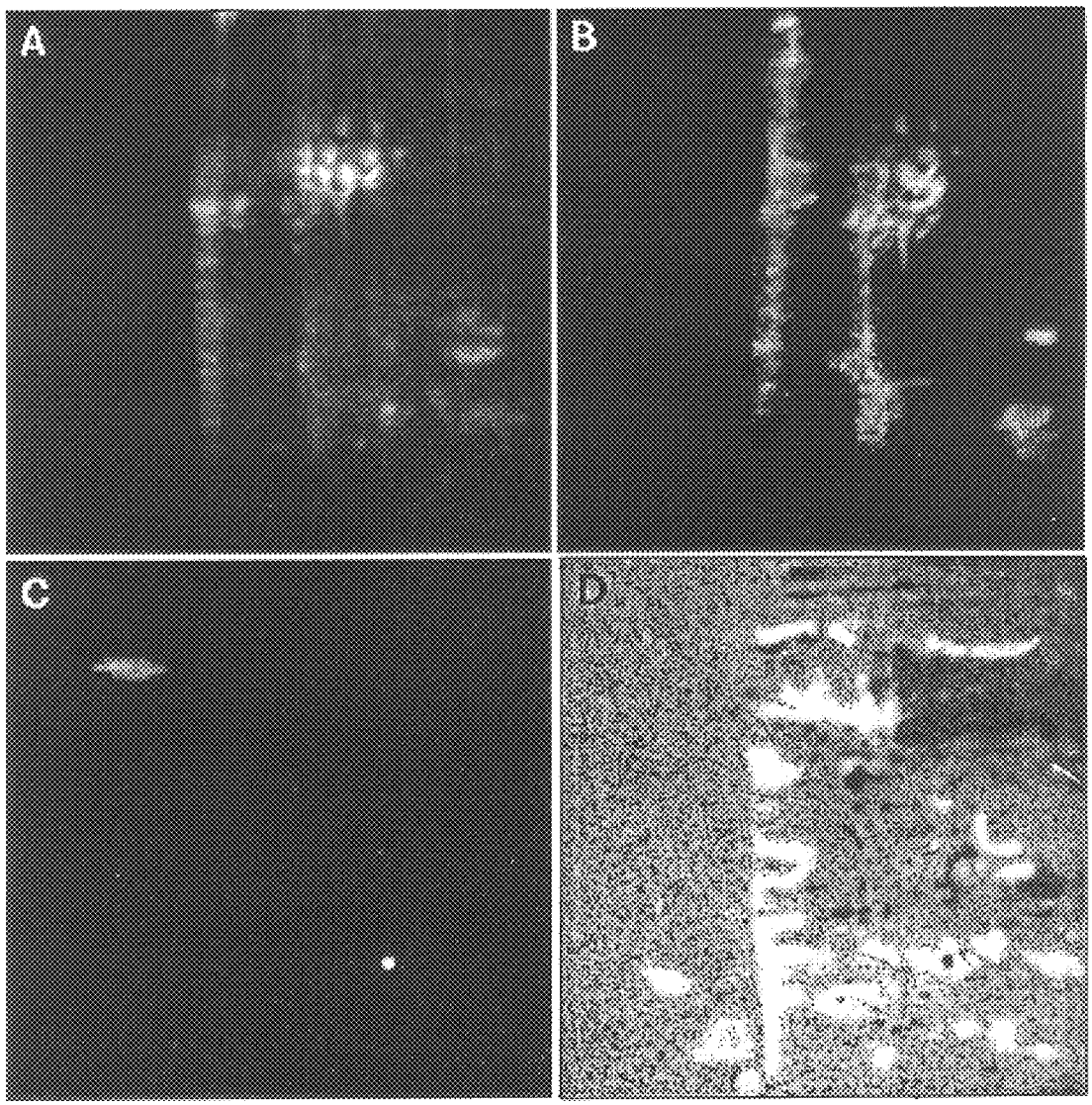
FIGS. 3 A, B, C and D are images of a portion of a two dimensional gel loaded with two different samples of bacterial extract, one IPTG-induced and the other uninduced, each labeled with a different one of the dyes of the matched pair of dyes according to the process of the present invention; and, FIGS. 4 A, B, C and D are images of a portion of a two dimensional gel loaded with two different samples of bacterial extract, one having exogenously added carbonic anhydrase and one without carbonic anhydrase, each labeled with a different one of the dyes of the matched pair of dyes according to the process of the present invention.

2. Difference two-dimensional gel electrophoresis of induced GAL4VP16 expression in bacteria:

FIG. 3 shows images of a portion of a two-dimension gel loaded with Propyl Cy-3 labeled IPTG-induced bacterial extract plus Methyl Cy-5 labeled uninduced extract.

Panel A. Images taken with Cy-3 excitation light showing the IPTG-induced proteins.

Panel B. Images taken with Cy-5 excitation light showing the uninduced proteins.

Panel C. Ratio of the Cy-3 image divided by the Cy-5 image.

Panel D. Overlay of the image in Panel C, colored red, and placed on top of the image from Panel B, colored blue.

Figure 4:
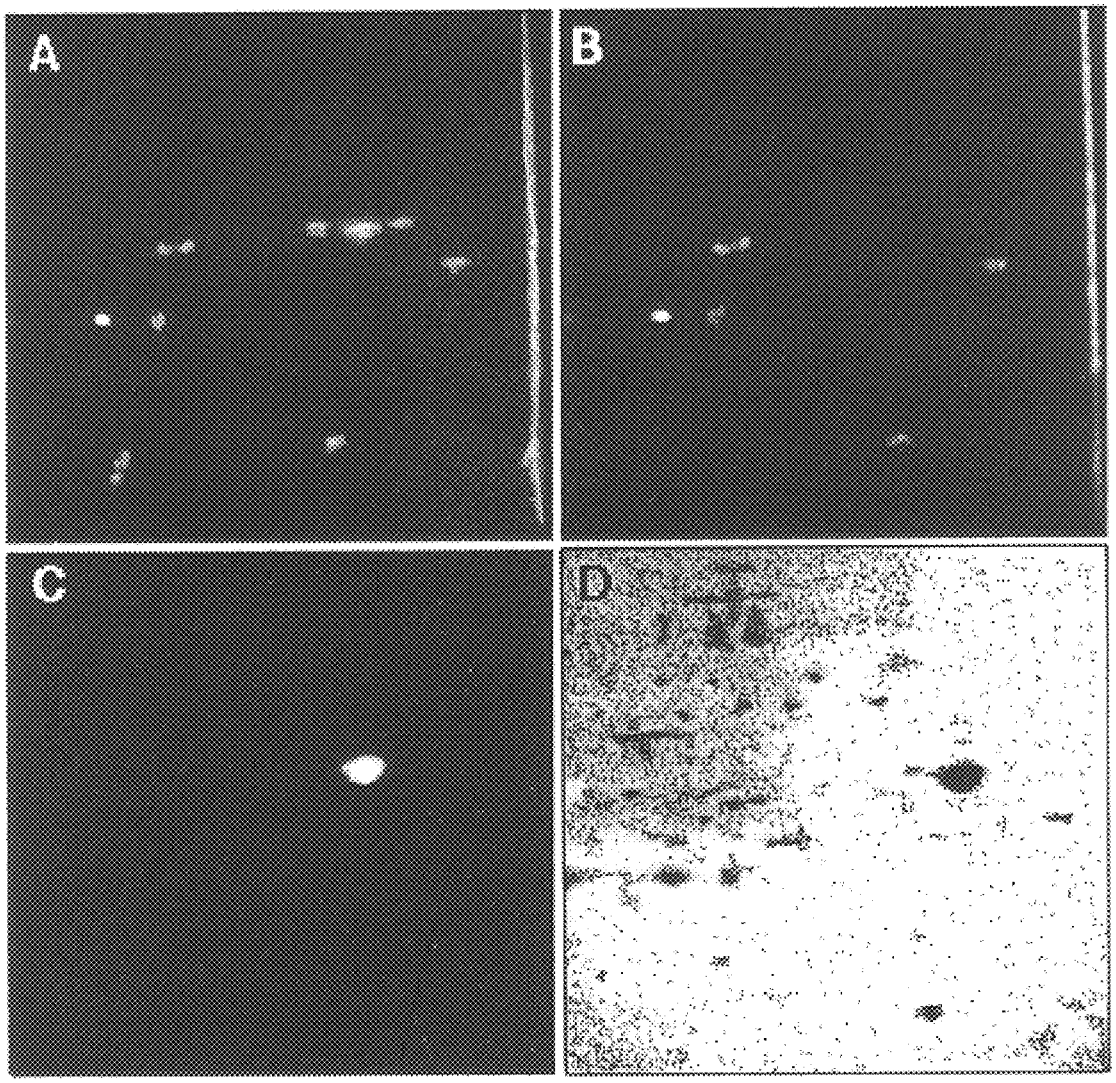

3. Difference two-dimensional gel electrophoresis of bacteria extract with exogenously added protein:

FIG. 4 shows images of a portion of a two-dimension gel loaded with Propyl Cy-3 labeled bacterial extract that had exogenously added carbonic anhydrase plus Methyl Cy-5 labeled extract without the added carbonic anhydrase.

Panel A. Image taken with Cy-3 excitation light showing the bacterial proteins plus carbonic anhydrase.

Panel B. Images taken with Cy-5 excitation light showing the bacterial proteins alone.

Panel C. Ratio of the Cy-3 image divided by the Cy-5 image.

Panel D. Overlay of the image in Panel C, colored red, and placed on top of the image from Panel B, colored blue.

The process of the present invention provides a simple and inexpensive way to analyze the differences in protein content of different cells. The process eliminates problems which can occur using two separate gels which must be separately electrophoresed. The matched dyes used to label the different cell extracts allow simultaneous electrophoresis of two or more different samples of cell extract in a single gel. While the invention has been described with reference to two samples of cell extract and a matched pair of dyes, those skilled in the art will appreciate that more than two samples may be simultaneously tested using an equal number of matched dyes. As long as the spectral characteristics of the dyes can be manipulated to provide fluorescence at a number of different wavelengths resulting in visually distinct images and the pH and ionic characteristics of the dyes can be generally equalized to compensate for changes made to the protein by virtue of covalent bonding to the dye, multiple dyes can be used.

What we claim is:

1. A method of comparing protein composition of interest between at least two different cell samples comprising:

(a) preparing an extract of proteins from each of said at least two cell samples;

(b) providing a set of matched luminescent dyes chosen from dyes capable of covalently binding to proteins within said extract of proteins, wherein each dye within said set (1) has a net charge which will maintain the overall net charge of the proteins upon such covalent binding and has ionic and pH characteristics whereby relative electrophoretic migration of a protein labeled with any one of said dyes is the same as relative electrophoretic migration of said protein labeled with another dye in said set,
(2) emits luminescent light at a wavelength that is sufficiently different from the emitted luminescent light of remaining dyes in said set to provide a detectably different light signal;
(c) reacting each extract of proteins of step (a) with a different dye from said set of step (b) to provide dye-labeled proteins;
(d) quenching the labeling reactions of step (c) between the dyes and the protein;
(e) mixing each of said dye labeled proteins to form a single mixture of different dye-labeled protein;
(f) electrophoresing the mixture of step (e) by a predetermined electrophoresing method capable of separation within said mixture; and
(g) detecting the difference in luminescent intensity between the different dye-labeled protein by luminescent detection.

2. The method of claim 1 wherein said dyes bind to a primary amine of a lysine residue of the protein and each said dye within said luminescent dyes carries a net +1 charge.

3. The method of claim 1 wherein said set of matched luminescent dyes are cyanine dyes having the following structure:

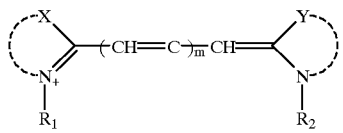

wherein the dotted lines each represent carbon atoms necessary for the formation of one to three fused rings having five to six atoms in each ring, X and Y are selected from the group consisting of S, O or $CH_3$—C—$CH_3$, m is an integer from 1 to 3, one of $R_1$ and $R_2$ is a reactive group and the other is an alkyl.

4. The method of claim 3 wherein said reactive group reacts with an amino in the protein and is selected from the group consisting of isothiocyanate, $(CH_2)_4COOH$ and $(CH_2)_4CON$-hydroxysuccinimidyl ester.

5. The method of claim 1 wherein said set of matched luminescent dyes are neutral dyes bound to the primary amino of a lysine residue in the protein by a positively charged linker group.

6. The method of claim 1 wherein said set of matched luminescent dyes are derivatives of dipyrromethene boron difluoride dyes having positively charged linker groups to bind the dye to the primary amino of a lysine residue in the protein.

7. The method of claim 1 wherein said dyes covalently bind to lysines in the proteins.

8. The method of claim 1 wherein said dyes covalently bind to sulfhydryl groups on the proteins.

9. The method of claim 1 wherein said dyes covalently bind to carboxylic acid groups on the proteins.

10. The method of claim 1 wherein the step of detecting differences in luminescent intensity is by fluorescent microscopy.

11. The method of claim 1 wherein the step of detecting differences in luminescent intensity is by electronic imaging.

12. The method of claim 1 wherein the proteins have binding sites for covalent binding to said dyes selected from the group consisting of lysine, carboxylic acid and sulfhydryl groups.

13. The method of claim 1 wherein the proteins binding sites for covalent binding to said dyes, and said binding sites are one of a moiety selected from the group consisting of lysine, carboxylic acid and sulfhydryl groups.

14. A method of comparing proteins of interest between at least two different samples comprising:
(a) preparing a mixture of proteins from each of said at least two samples;
(b) providing a set of matched luminescent dyes chosen from dyes capable of covalently binding to said proteins within said mixture of proteins, wherein each dye within said set
(1) has ionic and pH characteristics whereby relative electrophoretic migration of a protein labeled with any one of said dyes is the same as relative electrophoretic migration of said protein labeled with another dye in said set,
(2) emits luminescent light at a wavelength that is sufficiently different from the emitted luminescent light of remaining dyes in said set to provide a detectably different light signal;
(c) reacting each said mixtures of proteins of step (a) with a different dye from said set of step (b) to provide dye-labeled protein;
(d) quenching the labeling reactions of step (c) between the dyes and the proteins;
(e) mixing each of said dye labeled proteins to form a combined single mixture of different dye-labeled proteins;
(f) electrophoresing the combined mixture of step (e) by a predetermined electrophoresing method capable of separating the dye-labeled proteins of interest within said mixture; and
(g) detecting the difference in luminescent intensity between the different dye-labeled proteins of interest by luminescent detection.

15. The method of claim 14 wherein said set of matched luminescent dyes are cyanine dyes having the following structure:

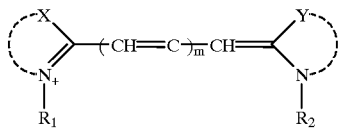

wherein the dotted lines each represent carbon atoms necessary for the formation of one to three fused rings having five to six atoms in each ring, X and Y are each selected from the group consisting of O, S and $CH_3$—C—$CH_3$, m is an integer from 1 to 3, one of $R_1$ and $R_2$ is a reactive group and the other is an alkyl.

16. The method of claim 15 wherein said reactive group is selected from the group consisting of and isothiocyanate, $(CH_2)_4COOH$ and $(CH_2)_4CON$-hydroxysuccinimidyl ester.

17. The method of claim 14 wherein said set of matched luminescent dyes are derivatives of dipyrromethene boron difluoride dyes having positively charged linker groups to bind the dye to the extract.

18. A method of comparing proteins of interest between at least two different samples comprising:
(a) preparing a mixture of proteins from each of said at least two samples;
(b) providing a set of matched luminescent dyes chosen from a single class of dyes capable of covalently binding to proteins within said mixture of proteins, wherein each dye within said set
  (1) has ionic and pH characteristics whereby relative electrophoretic migration of a protein labeled with any one of said dyes is the same as relative electrophoretic migration of said protein labeled with another dye in said set,
  (2) emits luminescent light at a wavelength that is sufficiently different from the emitted luminescent light of remaining dyes in said set to provide a detectably different light signal;
(c) reacting each mixture of proteins of step (a) with a different dye from said set of step (b) to provide dye-labeled proteins;
(d) quenching the labeling reactions of step (c) between the dyes and the proteins;
(e) mixing each of said dye labeled proteins to form a combined single mixture of different dye-labeled proteins;
(f) electrophoresing the combined mixture of step (e) by a predetermined electrophoresing method capable of separating the dye-labeled proteins of interest within said combined mixture; and
(g) detecting the difference in luminescent intensity between the different dye-labeled proteins of interest by luminescent detection.

* * * * *